United States Patent
Mahe et al.

(10) Patent No.: US 11,749,381 B2
(45) Date of Patent: Sep. 5, 2023

(54) IDENTIFICATION AND ANTIBIOTIC CHARACTERIZATION OF PATHOGENS IN METAGENOMIC SAMPLE

(71) Applicant: BIOMÉRIEUX, Marcy l'Etoile (FR)

(72) Inventors: Pierre Mahe, Lans en Vercors (FR); Maud Tournoud, Grenoble (FR); Stéphane Schicklin, Lyons (FR); Ghislaine Guigon, Dardilly (FR); Etienne Ruppe, Paris (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 1038 days.

(21) Appl. No.: 16/342,017

(22) PCT Filed: Oct. 12, 2017

(86) PCT No.: PCT/EP2017/076029
§ 371 (c)(1),
(2) Date: Apr. 15, 2019

(87) PCT Pub. No.: WO2018/069430
PCT Pub. Date: Apr. 19, 2018

(65) Prior Publication Data
US 2019/0252042 A1  Aug. 15, 2019

(30) Foreign Application Priority Data
Oct. 13, 2016 (EP) .................... 16193621

(51) Int. Cl.
*G16B 40/20* (2019.01)
*C12Q 1/689* (2018.01)
(Continued)

(52) U.S. Cl.
CPC ............. *G16B 40/20* (2019.02); *C12Q 1/689* (2013.01); *G16B 20/00* (2019.02); *G16B 30/00* (2019.02);
(Continued)

(58) Field of Classification Search
CPC ........ G16B 40/20; G16B 20/00; G16B 30/00; C12Q 1/689
(Continued)

(56) References Cited

U.S. PATENT DOCUMENTS 5,234,809 A  8/1993  Boom et al.
9,486,487 B2 * 11/2016  Cutcliffe .............. A61K 35/742
(Continued)

FOREIGN PATENT DOCUMENTS

CN  103186716 A  7/2013
WO  2014/144529 A1  9/2014

OTHER PUBLICATIONS

Truong et al.; "MetaPhlAn2 for enhanced metagenomic taxonomic profiling"; Nature Methods; vol. 12; pp. 902-903; 2015; and Erratum, vol. 13, pp. 101, 2016.
(Continued)

*Primary Examiner* — Olivia M. Wise
*Assistant Examiner* — Guozhen Liu
(74) *Attorney, Agent, or Firm* — Oliff PLC

(57) ABSTRACT

A method for identifying a pathogen contained in a metagenomic sample and for identifying pathogenic markers in the genome of the pathogen includes: processing the sample to extract DNA from pathogens, sequencing the extracted DNA, thereby producing a set of reads, comparing the reads to a database of genomes of known pathogens to assign reads to the pathogens; producing a pool of reads and assembling them to produce contigs, comparing the contigs to a second database of markers to check whether they contain a marker. The method further includes the step of comparing the reads to the second database to assign reads to the markers, a read being assigned to a marker if it falls entirely into or is astride the marker, and the pool also includes the reads assigned to the markers, the contigs
(Continued)

thereby being assembled from reads assigned to a pathogen and reads assigned to markers.

20 Claims, 4 Drawing Sheets

(51) Int. Cl.
- *G16B 20/00* (2019.01)
- *G16B 30/00* (2019.01)
- *C12Q 1/6888* (2018.01)

(52) U.S. Cl.
CPC ..... *C12Q 1/6888* (2013.01); *C12Q 2600/106* (2013.01); *C12Q 2600/158* (2013.01)

(58) Field of Classification Search
USPC .......................................................... 702/19
See application file for complete search history.

(56) References Cited

U.S. PATENT DOCUMENTS

| | | | | |
|---|---|---|---|---|
| 2005/0221341 | A1* | 10/2005 | Shimkets | G16B 30/10 702/20 |
| 2013/0310263 | A1* | 11/2013 | Lo | G16B 20/20 702/20 |
| 2015/0032711 | A1 | 1/2015 | Kunin | |
| 2015/0337362 | A1 | 11/2015 | Tarendeau | |

OTHER PUBLICATIONS

Guigon et al.; "Pathogen characterization within the microbial flora of bronchoalveolar lavages by direct sample sequencing"; ECCMID; pp. 1-17; 2015.
Oulas et al.; "Metagenomics: Tools and Insights for Analyzing Next-Generation Sequencing Data Derived from Biodiversity Studies"; Bioinformatics and Biology Insights; vol. 9; pp. 75-88; 2015.
Bolger et al.; "Trimmomatic: a flexible trimmer for Illumina sequence data"; Bioinformatics; vol. 30; pp. 2,114-2,120; 2014.
Simpson et al.; "Efficient de novo assembly of large genomes using compressed data structures"; Genome Research; vol. 22; pp. 549-556; 2012.
Wood, Derrick and Salzberg, Steven; "Kraken: ultrafast metagenomic sequence classification using exact alignments"; Genome Biology; vol. 15; pp. 1-12; 2014.
Li, Heng; "Aligning sequence reads, clone sequences and assembly contigs with BWA-MEM"; Genomics; vol. 00; pp. 1-3; 2013.
Jaillard et al.; "Optimization of alignment-based methods for taxonomic binning of metagenomics reads"; Bioinformatics; pp. 1-9; 2016.
Peng et al.; "IDBA-UD: a de novo assembler for single-cell and metagenomic sequencing data with highly uneven depth"; Bioinformatics; vol. 28; pp. 1,420-1,428; 2012.
Li et al.; "Megahit: an ultra-fast single-node solution for large and complex metagenomics assembly via succinct de Bruijn graph"; Bioinformatics; vol. 31; pp. 1,674-1,676; 2015.
Haider et al.; "Omega: an Overlap-graph de novo Assembler for Metagenomics"; Bioinformatics; vol. 30; pp. 2,717-2,722; 2014.
Boisvert et al.; "Ray meta: scalable de novo metagenome assembly and profiling"; Genome Biology; vol. 13; pp. 1-13; 2012.
Bankevich et al.; "SPAdes: A New Genome Assembly Algorithm and its Applications to Single-Cell Sequencing"; Journal of Computational Biology; vol. 19; pp. 455-477; 2012.
Afiahayati et al.; "MetaVelvet-SL: an extension of the Velvet assembler to a de novo metagenomic assembler utilizing supervised learning"; DNA Research; vol. 22; pp. 69-77; 2015.
Altschul et al.; "Basic Local Alignment Search Tool"; Journal of Molecular Biology; vol. 215; pp. 403-410; 1990.
Segata et al.; "Metagenomic microbial community profiling using unique clade-specific marker genes"; Nature Methods; vol. 9; 811-814; 2013.
Millan et al.; "Fecal Microbial Transplants Reduce Antibiotic-resistant Genes in Patients With Recurrent Clostridium difficile Infection"; Clinical Infectious Diseases; vol. 62; pp. 1,479-1,486; 2016.
Ju, Feng and Zhang, Tong; "Experimental Design and Bioinformatics Analysis for the Application of Metagenomics in Environmental Sciences and Biotechnology"; Environmental Science & Technology, vol. 49; pp. 12,628-12,640; 2015.
Elbehery et al.; "Antibiotic Resistome: Improving Detection and Quantification Accuracy for Comparative Metagenomics"; OMICS A Journal of Integrative Biology; vol. 20; pp. 229-238; 2016.
Rawat et al.; "MetaGeniE: Characterizing Human Clinical Samples Using Deep Metagenomic Sequencing"; PLOS One; vol. 9; pp. 1-12; 2015.
Ruppé et al.; "Clinical metagenomics of bone and joint infections: a proof of concept study"; Scientific Reports; vol. 7; pp. 1-12; 2017.
Kultimia, et al.; "MOCAT2: a metagenomic assembly, annotation and profiling framework"; Bioinformatics; vol. 32; pp. 2,520-2,523; 2016.
Luo, et al.; "SOAPdenovo2: an empirically improved memory-efficient short-read de novo assembler"; GigaScience; vol. 1; pp. 1-6; 2012.
Vervier, et al.; "Large-scale machine learning for metagenomics sequence classification"; Bioinformatics; vol. 32; pp. 1,023-1,032; 2016.
Jan. 12, 2018 Search Report issued in International Patent Application No. PCT/EP2017/076029.
Jan. 12, 2018 Written Opinion issued in International Patent Application No. PCT/EP2017/076029.

* cited by examiner

IDENTIFICATION AND ANTIBIOTIC CHARACTERIZATION OF PATHOGENS IN METAGENOMIC SAMPLE

FIELD OF THE INVENTION

The invention relates to the field of metagenomics, and in particular the characterization of antibiotic susceptibility of pathogens in metagenomic samples by asserting the presence of antibiotic resistance markers in their genomes.

BACKGROUND OF THE INVENTION

Currently, the identification and the Antibiotic Susceptibility Testing (AST) profiles of pathogens in a clinical sample by classical microbiology technics requires a lot of tests and/or a lot of a priori knowledge on the pathogens. For example, the microbiology workflow involves the growth of the pathogens (e.g. on a Petri dish) to isolate them and to get a critical biomass needed for subsequent tests. However different bacteria may require different culture conditions (e.g. aerobic vs. anaerobic bacteria), may compete during culture, or even may not grow at all if the culture conditions are not chosen in a proper manner. The choice of a culture medium is thus usually based on assumption about pathogens in the sample. In addition, tests requires pre-identification of a pathogens (e.g. Gram positive or negative) to choose the reagents of the AST. Robustness of microbiologic technics may be thus sometimes questionable.

In addition classical microbiology takes between 24 h to 48 h to get the identification and the Antibiotic Susceptibility Testing (AST) profiles of pathogens, even weeks for slow growing bacteria such as mycobacteria. During this period of time the clinician does not know which pathogen is infecting a patient and thus cannot provide any specific therapy. Not only patient's life may be at stake but it also forces the clinician to give the patient broad spectrum antibiotics before having the AST profile and adapting his therapy, which is one of the main reasons why bacteria develop antibiotic resistance mechanism over time.

In microbiology, metagenomics is a Nucleic Acid (NA) sequencing based technics which aims at characterizing the microorganism content of a sample using a linear workflow with less a priori information on this content. In particular, metagenomics does not involve the growth of bacteria for isolating them and the choice of a step in the metagenomic workflow does not depend on the results of the preceding steps. In addition, the workflow duration is substantially independent of the microorganisms contained in the sample and it is possible to process samples comprising a mix of different microorganisms (e.g. different bacterial species) and get at the same time the global picture of the microbiological content of the sample.

Recently quick and robust sequencing technics have been designed, in particular High Throughput Sequencing (HTS) (e.g. Whole Genome Sequencing (WGS), Next Generation Sequencing (NGS)) which may sequence large genomes precisely and rapidly. Based on these technics, a HTS metagenomic workflow consists in:
a. collecting a sample, for example a tissue or bodily fluid sample from a patient or animal (e.g. bronchalveolar lavage, blood, urine, saliva, faeces . . . ), a food sample or an environmental sample (e.g. air, water;
b. extracting nucleic acids (e.g. genomic DNA) from cells in the sample;
c. randomly shearing the nucleic acid molecules into smaller fragments and tagging the fragments for amplification and sequencing purpose;
d. at least the for second HTS generation, amplifying the fragments (e.g. by PCR based technics) to have multiples copies of each fragments, allowing in turn to get a readable signal from sequencing step;
e. sequencing the fragments, thereby producing a set of digital nucleic acid sequences (often called "raw reads" or "reads");
f. analyzing the reads to characterize the content of the sample (e.g. identifying the microorganisms in the sample) using a computer processing workflow (often called "bioinformatics pipeline" or "pipeline").

Basically, there are two types of pipeline for characterizing the sample content, a first type of pipeline using taxonomic binning, and a second type using profiling.

Many profiling pipelines have been developed during the last years to efficiently describe the taxonomic and/or the functional (genes content) composition of metagenomic samples. For example "MetaPhlAn2" (Truong et al., "MetaPhlAn2 for enhanced metagenomic taxonomic profiling", *Nature Methods,* 2015) is an efficient taxonomic profiling method, that relies on marker genes that are unique and specific to a given taxonomic clade. Briefly, reads are mapped against a marker genes reference database, allowing then to quantify all the taxonomic clades present in the sample. In a more recent taxonomic and functional profiling pipeline called "MOCAT2" (Kultima et al. "MOCAT2: a metagenomic assembly, annotation and profiling framework", *Bioinformatics,* 2016), reads are assembled using the "SOAPdenovo" assembler (Ruibang Luo et al. "SOAPdenovo2: an empirically improved memory-efficient short-read de novo assembler", GigaSicence, 2012), predicted, and annotated very efficiently against a combined catalogue of functional information from multiple databases (egg-NOG, KEGG, SEED, ARDB, CARD . . . ). Taxonomic and functional profiling may be used to first identify and get the relative proportion of pathogens, and also get ARD present in the sample.

Regarding, taxonomic binning based pipelines, they comprises an assignment step (also called "taxonomic binning") consisting in:
f1. assigning each read to a known taxon (e.g. a bacterial species) for which one or more representative genomes or portions of genome (e.g. 16S portion of the genomes) has been sequenced and stored in a reference database ("taxonomic database");
f2. in pooling the reads assigned to a taxon; and
f3. in assembling the pooled reads in order to reconstitute the taxon's genome, usually long sequences thereof, often called "contigs".

The contigs are then used for further characterization, in particular pathogen identification and search for Antibiotic Resistance Determinants (ARD) in the reconstituted genome(s). HTS technics thus allows to have access simultaneously to the set of pathogens present in a sample but also to the set of (ARD) contained in their genomes. However those technics cannot link ARD and pathogens, which is the main piece of information for a clinician who wants to know which pathogen is present in the sample, and which ARD (if any) this particular pathogen harbours. Furthermore, it is of interest for clinicians to get the sequence of the ARDs present in the sample. Indeed, antibiotic resistance may be due the presence or absence of resistance genes but also to the presence of specific resistance genes variants, and in this case it is crucial to have access to the most accurate sequences of the resistance determinants.

A first step to circumvent this problem is to apply the pipeline described in Guigon et al., ("Pathogen Characterization within the Microbial Flora of Bronchoalveolar Lavages by Direct Sample Sequencing", ECCMID, 2015), and called "Pipeline1" in the sequel of this document.

Briefly, the main steps are: quality control of the reads (filtering and trimming of reads with low quality), elimination of host DNA (filtering of human reads), taxonomic binning, assembly of reads corresponding to each pathogen present in the sample into "contigs", and finally annotation of the contigs with respect to an ARD reference database.

Unfortunately, the pipeline described above does efficiently derive links between pathogens and ARD only when said links are explicitly coded in the reference databases. FIG. 1 illustrates a typical case of failure. A metagenomic sample includes DNA from a bacterial species ("species 1") which harbours a resistance gene. As many resistance genes in bacteria, the considered gene is located on a Mobile Genetic Element (MGE). MGEs are a type a DNA moving around between bacterial genomes and are an important source of genetic variability, and thus antibiotic adaptation capability of bacteria. Unfortunately, in the reference database used for taxonomic binning, none of the representative genome of Species 1 harbours this ARD, contrary to representative genomes of other species ("Species k"). This might happen, precisely because this ARD is located on a MGE. For example the micro-organism from Species 1 present in the sample under study might have acquired it recently from a strain of Species k, although this transfer has not been observed yet in the reference sequences used to build the Reference Database for taxonomic binning Thus, during the taxonomic binning step, reads located in the ARD region of Species 1, will not be retrieved with the other reads of Species 1 since those they will be set apart as representative of Species k. Thus the assembly of Species 1 will lead, in the best case, to 2 contigs, and the ARD will be missing from the assembly.

In other words, reference databases are a static snapshot of the knowledge available at a moment regarding pathogens. For prior art pipeline, the only way to take into account genomic modification of pathogens in connection with ARD is to update the databases. At least for the first time a clinician is facing a new pathogen, prior art metagenomic analysis is helpless in characterizing the antibiotic sensibility of the pathogen, and even worse, may be misleading by rendering a false result, e.g. in the aforementioned example species k as the resistant pathogen rather than species 1.

Moreover, when an ARD is shared by several pathogens, many prior art taxonomic binning approaches assign the corresponding reads to the Lowest Common Ancestor of the pathogens that harbor the ARD. Thus, reads corresponding to the ARD will not be retrieved during the taxonomic binning step, because they will be assigned at a higher level than a "Species level". To retrieve them, one will have to define specific rules to retrieve reads at the Species, based on the classification at a higher level (e.g. if a read is assigned at the Genus level G, add the read to all the pools of reads of all the species included in Genus G).

While the problematic has been illustrated in connection with antibiotic resistance determinants ARD, it applies in the same way to virulence genetic determinants. This problematic also applies for other types microorganisms, like for example fungus and antifungal resistant determinant.

More generally, this problematic applies to any type of genomes, form any type of source, for which one looks for genetic markers of interest, which markers are absent from the genomes of the species they come from in the reference database.

SUMMARY OF THE INVENTION

The present invention proposes a new metagenomic analysis which allows to take into account genetic modification in markers of interest using reference database which does not reference those modifications.

To this end, an object of the invention is a method for identifying a pathogen (e.g. bacterium) contained in a metagenomic sample and for identifying pathogenic markers (e.g. antimicrobial susceptibility, virulence, . . . ) in the genome of said pathogen, the method comprising the step of:
  processing the metagenomic sample to extract DNA at least from pathogens present in said sample,
  sequencing the extracted DNA, thereby producing a set of digital nucleic acid sequences, or "reads",
  comparing the set of reads to a first database comprising genomes of known pathogens in order to assign reads of said set to the known pathogens;
  producing a pool of reads comprising at least reads assigned to a pathogen amongst said known pathogens and assembling the reads in the pool in order to produce at least one assembled digital nucleic acid sequence, or "contig",
  comparing the produced contigs to a second database of known pathogenic genetic markers in order to check whether the produced contigs contain a known marker.

According to the invention:
  the method comprises the step of comparing the set of reads to the second database in order to assign reads of said set to the known pathogenic markers, a read being assigned to a known pathogenic marker if it falls entirely into said marker or if it is astride said marker,
  and the pool also comprises the reads assigned to the known pathogenic markers, the contigs being thereby being assembled from reads assigned to the known pathogen and reads assigned to the known pathogenic markers.

In other words, the present invention takes advantage of the shearing step describe above. In one hand, the sample comprises several individuals of each pathogen. For example, for a given pathogen, there are several copies of DNA molecules resulting from the extraction process. On the other hand, as it is well known in the HTS technics, these copies are not fragmented identically on purpose, thereby producing overlapping fragments, the overlap feature being thereafter use for the assembly step. Hence by pooling together reads assign to a pathogen together with reads assigned to genetic marker, while some of said reads maps only partially on the marker, and thus also maps on phatogen's genome, the assembly process has the opportunity, for said pathogen, to construct contigs comprising the marker. This feature enables the reconstruction of genomes with markers that are different from the representative genomes in the taxonomic database.

FIG. 2 illustrate the invention applied to the sample described in FIG. 1, namely a sample with majority DNA from a strain of Species 1 which harbours an ARD located on a GME while the taxonomic database does not store any representative genome having such a feature for Species 1. Reads falling in the ARD region are retrieved by mapping reads against an exhaustive ARD database, and reads falling outside the ARD are retrieved by taxonomic binning of reads against the taxonomic database. Then, for each pathogen found in the sample (here only Species 1), reads identified as Species 1 and reads mapping against the ARD are pooled together to be assembled. Because of the "clipping" feature of the reads, i.e. the fact that some reads does not align on their entire length when mapping against the ARD database, the reads falling in the junction between the chromosome of Species 1 and the ARD (reads represented as dotted segments in FIG. 3) will also be retrieved. Such reads enable for the assembly to be complete, i.e. for the ARD to be integrated into the chromosome of Species 1 (see assembly in FIG. 2).

According to one embodiment, at least the portions of reads falling inside the markers have a length greater or equal to 20 bp, preferably greater or equal to 25 bp, more preferably greater or equal to 50 bp. In other words, standard assemblers succeed in assigning a read to a known pathogen genome or a marker with a good probability even when only a small portion of said read aligns with the ARD database.

According to one embodiment, the reads have an average length of L bp, with L>75, and reads that are astride said marker have a portion falling outside said marker in the range [1; L-55] bp. According to one embodiment, the reads have an average length of L bp, with L>100, and reads that are astride said marker have a portion falling outside said marker in the range [1; L-80] bp. According to one embodiment, the reads have an average length of L bp, with L>100, and reads that are astride said marker have a portion falling outside said marker in the range [1; L-50] bp.

According to one embodiment, the reads that are astride said marker have a first portion falling into said marker and a second portion falling outside said marker, and wherein the length of the second portion is chosen based on mapping against ARD database performance, in particular maximized while still maintaining a correct mapping performance (acceptable proportion of reads to the correct ARD). In one embodiment, the length of the second portion is chosen such that the probability of good alignment with the ARD database, or probability to get a "true hit", is greater or equal to 70%, preferably greater or equal to 80%.

According to one embodiment, the comparison of the set of reads with the second database comprises the mapping of each reads on the pathogenic markers of the second database, independently from the other reads of said set.

According to one embodiment, the sequencing is a paired-end sequencing, and if a read is assigned to a marker, a read which it is the complementary of said read is also included in the pool.

According to one embodiment, if a produced contig comprises only reads assigned to a known marker, said known pathogenic marker is determined to be part of the known pathogen's genome if:

$$D_{ARD} \in \left[\frac{1}{3} \times D_{path}; 3 \times D_{path}\right]$$

where $D_{ARD}$ is a median sequencing depth of the reads assigned to the known marker and $D_{path}$ is a median sequencing depth of the reads assigned to the known pathogen. and preferable >1

According to one embodiment, the method further comprises a step of comparing the contigs to 16SrDNA sequences and/or metaphlan2 markers, and wherein the known pathogen is confirmed based on said comparison.

According to one embodiment, the sample is taken from a human or an animal, and wherein the first database comprises also flora and host genomes, and wherein reads assigned to flora and host genomes are filtered out.

According to one embodiment, the metagenomic sample is a brochoalveolar lavage sample, an urine sample or a blood sample.

According to one embodiment, the pathogenic marker are antibiotic resistance markers or virulence makers.

Another object of the invention is a computer readable medium storing instruction for executing a method performed by a computer, the method comprising
  comparing a set of reads, produced by a sequencing of extracted DNA from a metagenomic sample, to a first database comprising genomes of known pathogens in order to assign reads of said set to the known bacterial pathogens;
  producing a pool of reads comprising at least reads assigned to a pathogens amongst said known pathogens and assembling the reads in the pool in order to produce at least one assembled digital nucleic acid sequence, or "contig",
  comparing the produced contigs to a second database of known pathogenic genetic markers in order to check whether the produced contigs contain a known marker,
  According to the invention
  the method comprises the step of comparing the set of reads to the second database in order to assign reads of said set to the known pathogenic markers,
  and the pool also comprises the reads assigned to the known markers, the contigs being thereby being assembled from reads assigned to the known pathogen and reads assigned to the known pathogenic markers.

Said computer readable medium stores instruction for executing the aforementioned method.

BRIEF DESCRIPTION OF THE DRAWINGS

The invention will be better understood from the following non-limiting description, in connection with the accompanying drawings, among which.

DETAILED DESCRIPTION

An embodiment of the invention is now described in connection with characterization of pathogens, in particular of Ventilarory Acquired Pneumonia (VAP), contained in a (mini)Broncho Alveolar Lavage (BAL) from patients in Intensive Care Unit (ICU). The objective is to list all the pathogens present in the sample, as well as antibiotic resistance determinant, and if possible link ARD to pathogens.

Figure 1:
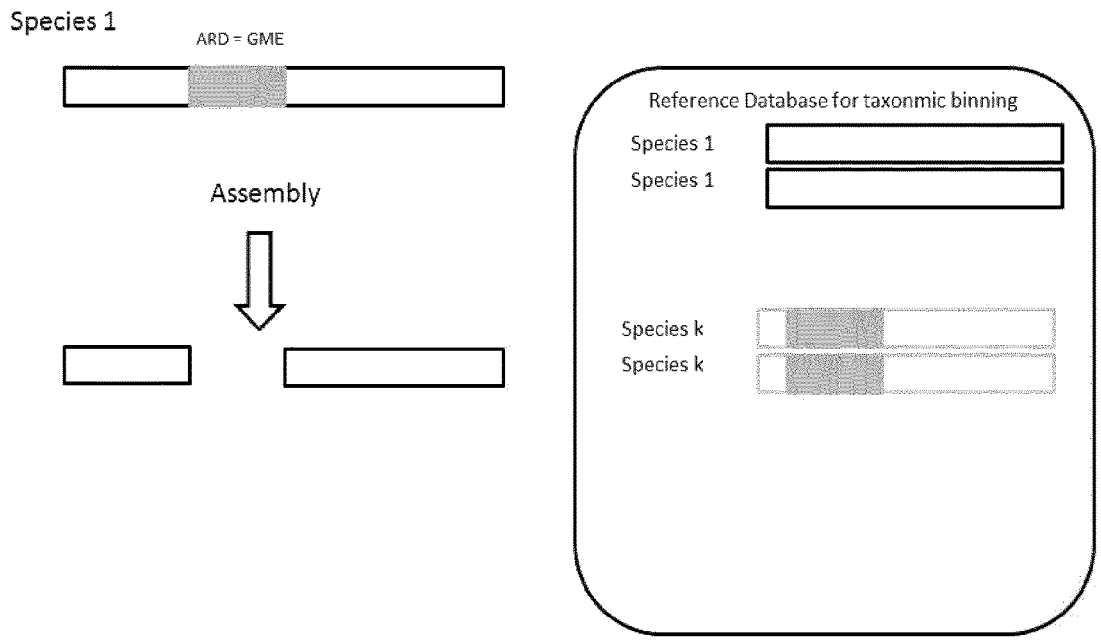
FIG. 1 illustrates limits of prior art taxonomic based pipeline to retrieve ARD located on Mobile Genetic Elements (MGE)
Figure 2:
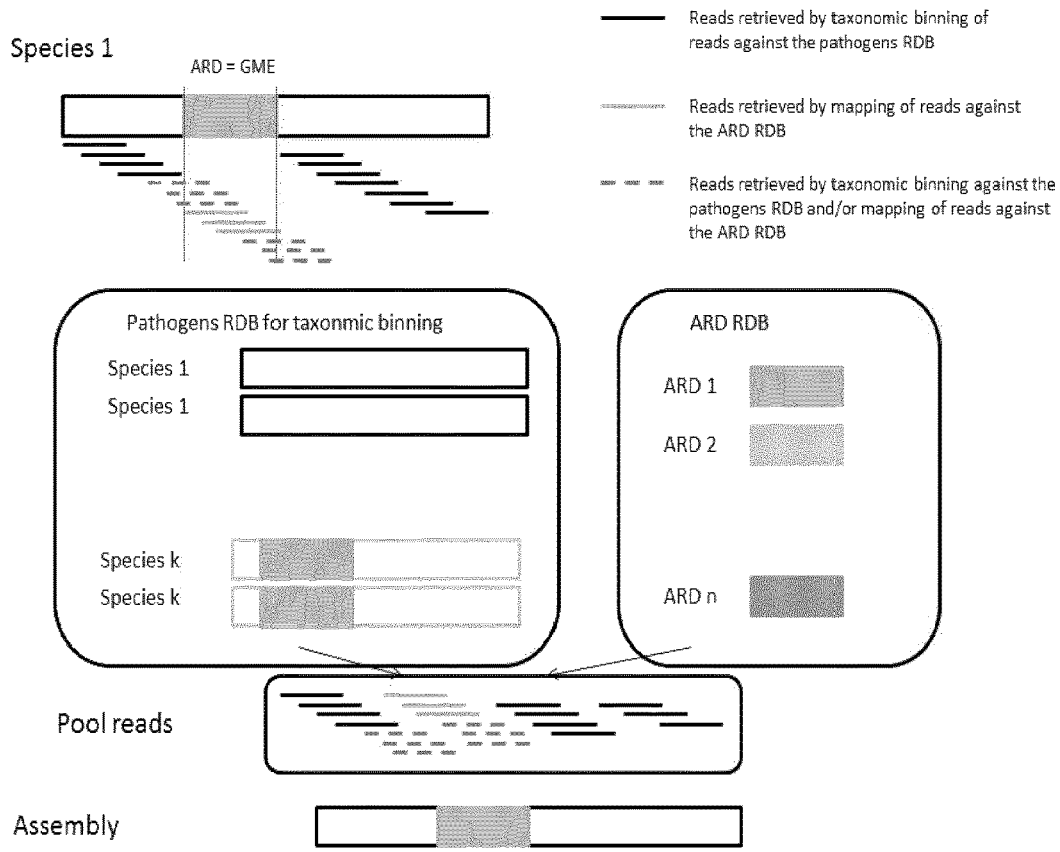
FIG. 2 illustrates the ability of the pipeline according to the invention to retrieve and ARD while reference databases does not code this feature, in particular in the case of ARD located on MGE.
Figure 3:
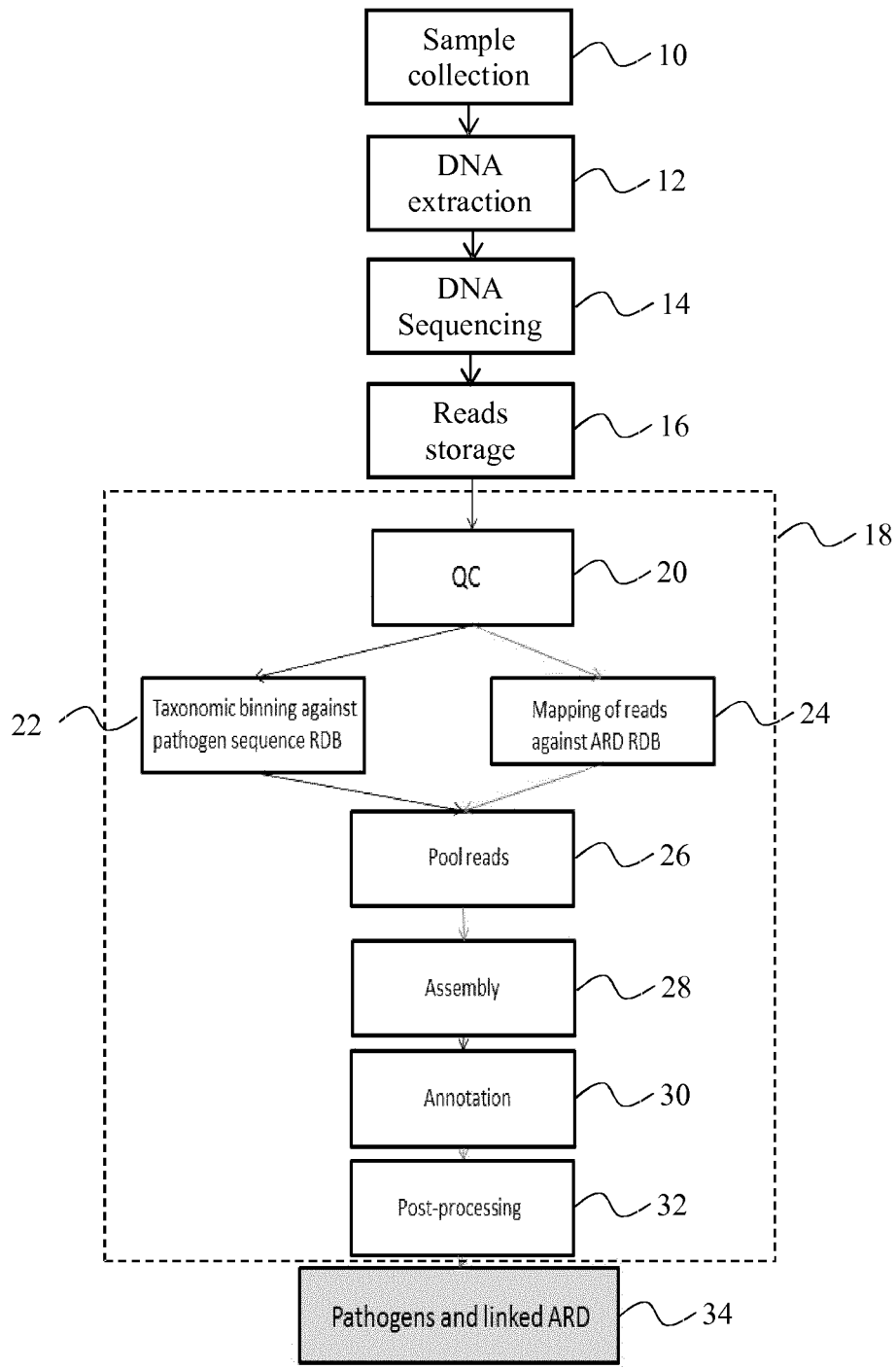
FIG. 3 is a flow chart of a metagenomic method according to the invention.

Referring to FIG. 3, a BAL sample is collected from a patient, in 10, and thereafter process in 12 for nucleic acid extraction from pathogens contained in the sample. This preparation comprises successively, by way of example:
- a host cell removing step by means of a saponin formulation, as described for example in document US 2015/0337362;
- a lysing step, for example a mechanical, enzymatic or osmotic lysis, which breaks down membranes of the cells in the sample, thereby releasing their acid nucleic content, breaking proteins by adding protease and breaking RNA by adding RNase;
- a filtering step consisting in adding concentrated salt to clump together protein, lipids and RNA, and in centrifuging for eliminating the clumped debris; and
- a purifying step for collecting DNA content, for example using Boom® technology based on magnetic silicate beads as described for instance in document U.S. Pat. No. 5,234,809, ethanol precipitation, phenol-chloroform extraction or minicolumn purification;

The extracted DNA is thereafter sequenced in 14 using whole genome sequencing HTS technics, e.g. a shotgun technic comprising:
- a library preparation step consisting in randomly shearing the NA molecules in fragments of 150-300 pairs of bases (bp), e.g. 250 bp;
- an amplification step of the fragments, e.g. by Polymerase chain reaction (PCR) (solid-phase bridge amplification, bead emulsion amplification, . . . );
- sequencing step for determining the sequence of bases in the fragments.

A set of reads is thereby produced and stored in 16 in a memory of a computer system.

The DNA sequencing is preferably carried out using HTS technics which reads both ends of the fragments, for example using Illumina® dye sequencing, for instance Miseq WGS paired-end sequencing technics, as described for example in Oulas et al., "Metagenomics: Tools and Insights for Analyzing Next-Generation Sequencing Data Derived from Biodiversity Studies", *Bioinform Biol Insights,* 2015. Having both ends of the reads sequenced makes assembly of the reads easier, and in particular facilitate incorporation of an ARD in the genome of a particular pathogen in the case of the taxonomic database does not include representative genomes with the ARD.

A bioinformatics pipeline 18 according to the invention is then run on the reads to list the pathogens in the sample and figure out if their genomes harbor antibiotic resistance determinants.

A first step 20 of the pipeline 18 consists in a preprocessing of the reads (usually called "Quality Control" (QC)), namely:
- a processing to eliminate reads corresponding to adapters ligated to the DNA fragment for the sequencing purpose and primers used for the amplification. For example regarding Illumina® technology, "Trimmomatic" tool is used (Bolger et al., "Trimmomatic: A flexible trimmer for Illumina Sequence Data", *Bioinformatics.* 2014);
- a processing to correct calling errors in the reads, or eliminate reads too corrupted, for example using the error correction module of the "String Graph Assembler" (SGA) tool (Simpson and Durbin, "Efficient de novo assembly of large genomes using compressed data structures", *Genome Research,* 2012).

Pipeline 18 goes on in 22 with:
- a taxonomic binning of the remaining reads against a taxonomic database that includes: a) reference genomic sequences of pathogens that are commonly responsible for ventilarory acquired pneumonia (e.g. *S aureus, S pneumoniae, E coli, K pneumoniae,* . . . ); b) reference genomic sequences of bacteria that are commonly found in the oropharyngeal flora; and c) reference genomic sequences of human,
- the selection of the reads that are assigned to pathogens, thereby eliminating reads that are assigned only to flora or human.

For the taxonomic binning, two approaches may be embodied, e.g. a compositional approach such as the "Kraken" tool (Wood and Salzberg, "Kraken: ultrafast metagenomic sequence classification using exact alignments", *Genome Biology,* 2014), or "Wowpal Wabbit" tool (Vervier et al., "Large-scale machine learning for metagenomics sequence classification", *Bioinformatics,* 2015), or a comparative approach, such as the "BWA-MEM" tool (Li, "Aligning sequence reads, clone sequences and assembly contigs with BWA-MEM", *Genomics,* 2013). Preferably, a read is assigned to a pathogen if it maps entirely in a representative genome of this pathogen stored in the taxonomic database.

Pipeline 18 also comprises a mapping 24 of each read against an ARD reference database that includes ARD of interest. In particular, a read is assigned to an ARD if:
- is assigned to an ARD if
- if the read maps entirely on the ARD; or
- if the read is astride the ARD and the portion of the ARD that maps on the ARD is sufficient to assign the read to the ARD; or
- in case of paired-end sequencing, if one read of the pair falls entirely or astride the ARD, the second read is automatically assigned to the ARD.

Figure 4:
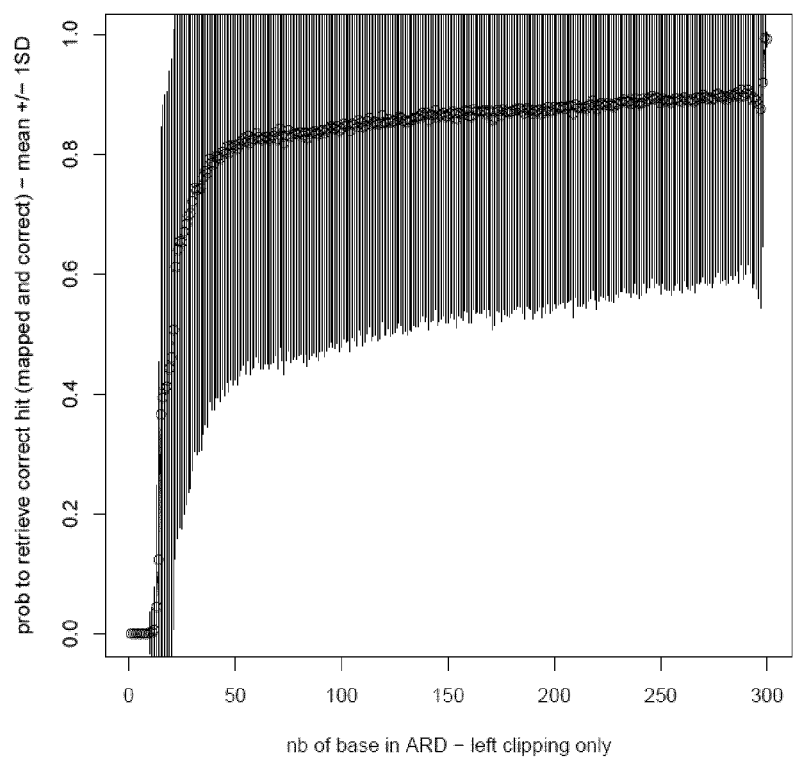
FIG. 4 illustrates the performance of BWA-MEM for ARD reads mapping against the ARD database, in particular the probability to retrieve the correct variant for reads with increasing number of bases in the ARD.

FIG. 4 illustrates the probability to retrieve an ARD for a read falling in the ARD, according to the number of bases of the read in the ARD. As one notes, a length of 50 bp that maps on an ARD is sufficient to precisely assign a read to this ARD (or, in other words, a length of 50 bp is sufficient to determine that a read comes from a genome portion having the ARD). It has been showed that the probability to retrieve a read in an ARD was 80% for reads with 250 bp outside the ARD and 50 bp in the ARD, 83% of the read outside the ARD. In this particular example, reads with a portion outside the ARD having a length in the range [0, L-50] bp are thus assigned to the ARD, L being the length of the ARD. For instance, with an average read length over 100 bp, reads with a length outside the ARD over 50 are assigned to ARD.

Usually, computational tool like "Kraken" and "Vowpal Wabbit" cannot find reads which are astride reference sequences because they do not allow clipping (that is to say authorizing a read to be assigned when it is astride). A comparative tool, such as "BWA-MEM", is thus used because it has a non-default mode authorizing clipping. However, said tool does not have a parameter for setting the length outside de ARD ("clipped length") or the length inside the ARD ("mapping length"). Those lengths however depend on BWA-MEM setting parameters. The setting of those lengths is thus done by:
- varying the setting parameters of BWA-MEM, for example using the experimental approach described in Jaillard et al., "Optimization of alignment-based methods for taxonomic binning of metagenomics reads", *Bioinformatics* 2016;

checking the clipped and mapping lengths derived from the parameter setting, and the percentage of reads that are successfully assigned to ARD(s);

choosing the parameters values of BWA-MEM that allows the greatest clipped length with a percentage of successively retrieve ARD over 70%, preferably over 80%.

For instance, BWA-MEM is run with the non-default parameters "-a -T 0 -k 16 -L 5 -d 100", leading to read assigned to ARD having clipped lengths in the range [0, L-50] bp.

In a preferred embodiment, the reads are mapped independently against the ARD database, even if the reads are paired because of the technics used for sequencing the DNA fragment (e.g. WGS paired-end sequencing technics). As it is well-known, in prior art assignment step, a read is usually assigned to an ARD not only if it maps against the database but also when its counterpart read maps. However, if one only keep reads that map "in a proper pair", meaning that both reads of the pair map on the ARD database, one only gets paired-end reads with an insert size smaller than a typical ARD length (~1000 bp). For example, in FIG. 5 only "read2.1". and "read2.2" would be retrieved as mapped in a proper pair, because they both fall in the ARD. When mapped independently, "read1.1", "read2.1", and "read2.2" are also retrieved.

Figure 5:
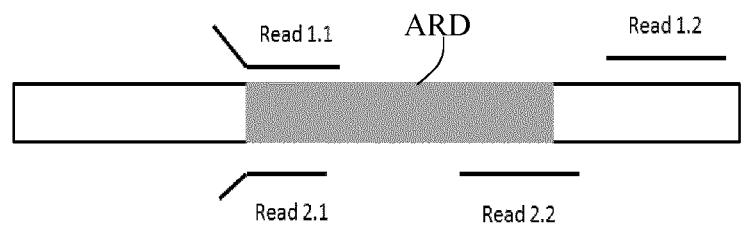
FIG. 5 illustrates Reads mapping against a ARD database.

Advantageously, when a read maps on an ARD, its counterpart read is automatically assigned to this ARD. In the example of FIG. 5, "read 1.2", which does not map on the ARD, is thus automatically assigned to the ARD because "read 2.2" does. "Read 1.2" is particularly useful because it falls in a chromosomic region of a pathogen, and together with reads retrieved by taxonomic binning it can be used to reconstruct the whole region, the chromosome and the ARD, as it will described latter.

Pipeline 18 goes on with a pooling step 26. In particular, for each pathogen associated to reads, a pool of reads is created, said pool comprising the reads assigned to said pathogen and all the reads assigned to ARD(s). As mentioned above, if one read of a pair maps against the ARD database, the other read is included automatically in the pool because it has been assigned also to the ARD database. Given that current assemblers do not perform well with too low or too high sequencing depth, only pathogen with average sequencing depth greater or equal to 3 are considered for assembly. When sequencing depth is larger than 150, a random set of pathogen reads is selected amongst the whole set of reads assigned to said pathogen to have a final average sequencing depth equal to 150.

An assembly step 28 is then carried out for each created pools of reads in order to produce contigs. For instance, the assembly step runs "de novo" assemblers such as "IDBA-UD" (Peng et al., "IDBA-UD: a de novo assembler for single-cell and metagenomic sequencing data with highly uneven depth", *Bioinformatics*, 2012), "MegaHit" (Li et al., "MEGAHIT: an ultra-fast single-node solution for large and complex metagenomics assembly via succinct de Bruijn graph.", *Bioinformatics*, 2015), "Omega" (Haider et al., "Omega: an Overlap-graph de novo Assembler for Metagenomics", *Bioinformatics*, 2014), "Ray Meta" (Boisvert et al., "Ray Meta: scalable de novo metagenome assembly and profinling", *Genome Biology*, 2012), "Spades" (Bankevich et al., "SPAdes: a new genome assembly algorithm and its applications to single-cell sequencing.", *Journal of Computational Biology*, 2012), or "Meta-Velvet-SL" (Afiahayati et al., "MetaVelvet-SL: an extension of the Velvet assembler to a de novo metagenomic assembler utilizing supervised learning", *DNA Reasearch*, Oxford journal, 2012). One notes that the assembly is done on pools of reads corresponding each corresponding to a unique pathogen, and not directly on whole metagenome with several micro-organisms. Given that, IDBA-UD and Spades gives the best performance and are thus preferred. The parameters for IDBA-UD and Spades are for example default parameters, that is to say respectively "idba ud500 --mink 40 --maxk maxReadLength --min_pairs 2" and "spades.py --careful --coy-cutoff 3".

Assembly step 28 thus transforms each pool of reads in a set of contigs (usually named "assembly"), preliminary assigned to a particular pathogen of the taxonomic database, which contigs may comprise one or more ARD.

In a preferred embodiment, the assembly step comprises the following steps: a) reads are first pre-processed with SGA (if it was not performed in QC step 20), b) then assembled using a de novo assembler, c) and original reads are mapped against contigs to polish the assembly (i.e. remove ultimate assembly errors). In particular, a contig is discarded if none of the pairs of reads maps against it.

A following step 30 of the pipeline 18 consists in confirming the identity of pathogens based on the sets of contigs and identifying the ARD in the genome of the identified pathogen(s). In particular, for each set of configs, the following step are carried out:

a species confirmation. To do so, presence of 16S rDNA gene (which are part of the taxonomic database since comprised in the genome of the pathogens) is searched for in each assembly, for instance using the "BLAST" alignment algorithm (Altschul et al., "Basic local alignment search tool", *Journal of molecular biology*, 1990). If a 16S rDNA gene copy is found in a contig, it is check whether the best hit corresponds to the pathogen identified at the taxonomic binning step 22. In case of several copies of the 16S rDNA gene in the assembly, it is checked whether at least one of the best hits corresponds the pathogen identified in step 22. In case a) no 16SrDNA copy is found in the assembly or b) a 16SrDNA copy does not correspond to the pathogen associated to the assembly, said assembly is discarded from the main pipeline analyze. In case a. the assembly is however kept in memory for further investigation. This conservative decision avoids to miss pathogens present in small quantity and for which the assembly is probably not complete;

an identification of ARD. To do so, each assembly is analyzed for the presence of ARD(s) listed in the ARD database, for instance using the BLAST alignment algorithm to identify the ARD present in the contigs. For each ARD, at least the best hit is reported.

Rather than 16SrDNA sequences, "Metaphlan2" markers are used for identity confirmation, those markers being described for example in Segata et al., "Metagenomic microbial community profiling using unique clade-specific marker genes", *Nature Methods*, 2012.

A final processing step 30 is then carried out to process the identified ARDs in order to link them to pathogens. In each assembly, the origin of reads mapping against the contigs annotated with an ARD is analyzed. If some of the reads that map on a contig with an ARD are obtained from the taxonomic binning against pathogen RDB (step 20), thus the ARD is definitively linked to the pathogen. In practice, at least 5% of the total number of reads mapping against the contigs containing an ARD are required to come from step 20.

Figure 6:
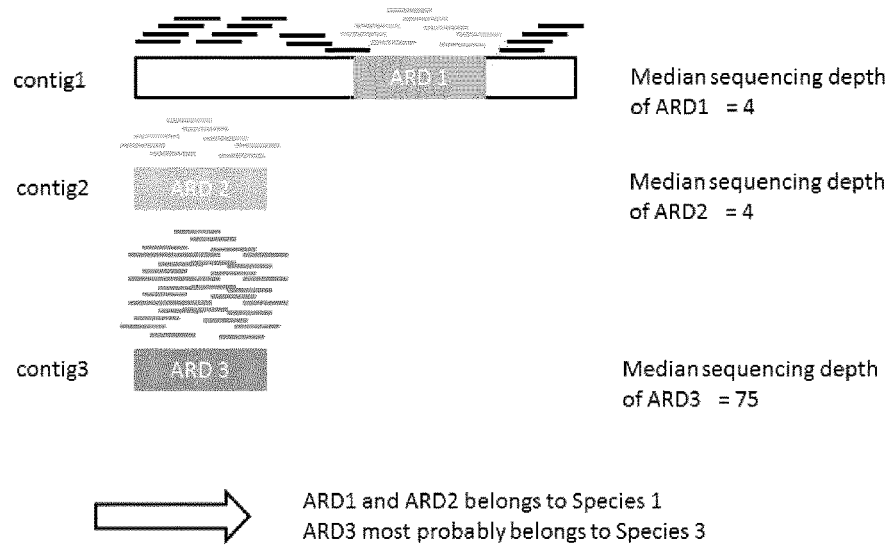
FIG. 6 illustrates a post processing of the ARD to link them to pathogens.

The assembly may however comprise ARD contigs that are not derived from step 20. For example, referring to FIG. 6, in case of "contig2" and "contig3", all the reads mapping on the contigs are obtained from the mapping of the reads against ARD database (step 24). Thus, it is not possible to formally link the ARD and the pathogen. A first reason rests on the fact that the ARD is not part of the pathogen's genome. However, those contigs may actually corresponds to the pathogen genome. Indeed it may happen that the ARD is located on a particular MGE, that is to say a plasmid. In such case, by definition, the ARD is not integrated in the contigs corresponding to the chromosome of the pathogen, but constitute an independent contig. In a preferred embodiment, the processing step 30 links the ARD to the pathogen with a smaller evidence by comparing the median sequencing depth of the ARD ($D_{ARD}$) and the median sequencing depth of the pathogen ($D_{path}$), the median sequencing depth being the median of the distribution of the number of reads that map on the assembly each position (obtained at step c. of assembly step 28). $D_{ARD}$ is the median of the distribution of the number of reads that map at each position of an ARD, and $D_{path}$ is the median of the distribution of the number of read that map at each position of the assembly of the pathogen. In particular, an ARD is linked to the pathogen(s) with the closest average sequencing depth. In the example of FIG. 6, "ARD2" located on "contig2" should be assigned to "Species 1" (because the median sequencing depth of "contig2" is 4 and the median sequencing depth of "Species1" is 4), while "ARD3" located on "contig3" should be assigned to "Species2" (because the median sequencing depth of "contig3" is 75 and the median sequencing depth of "Species" 2 is 8.). In practice, the ARD is assigned to all the species that have a median sequencing depth between 1/3 and 3 of the ARD median sequencing depth, and preferably greater than 1 because an ARD may be present in several copies in the genome of the pathogen.

Finally, the metagenomics analysis ends with an information/storing step 34 comprising the storage of the results of the pipeline 18, in particular, the list of identified pathogens and the ARD linked thereto, and/or the display of those results on a screen of a computer.

Validation Study

Three validation studies of the metagenomic analysis according to the invention have been done. The first validation study relies on in silico simulated metagenomes (validation study 1), the second validation study is a set of 3 positive miniBAL metagenomic samples for which only the culture identification is available (validation study 2), and the third validation study is a set 2 positive BAL metagenomic samples with identification and AST profiles available (validation study 3). For all the evaluation, Kraken is used for taxonomic binning and ARD binning (steps 22, 24) and IDBA-UD is used for assembly (step 28).

Validation Study 1

21 metagenomes have been simulated, each including 1 of the 21 selected pathogens (see Table 1). Each metagenome contains 300000 read pairs from the main pathogen, and 15000 read pairs from flora genomes. Genomes used for the simulations are real public genomes. Reads are simulated according to the Illumina MiSeq error model, with 2*300 bp paired-end reads, with V2 chemistry. Table 1 presents the strain used for the 21 simulated metagenomes, the number of ARD present in each strain, the number of ARD that are retrieved by the prior art pipeline ("P1"), and the number of ARD that are retrieved by the pipeline according to the invention ("P1+2"). Results are clearly in favor of the new pipeline which enables in most cases to recover all the ARD that were present in the original genomes.

TABLE 1

Table 2: Simulated strains and number of ARD found in the genomes of origin, in the assembly with IDBA-UD after P1 only, and in the assembly with IDBA-UD after P1 + P2.

| Strain | # ARDs in the strain | # ARDs retrieved by P1 only | # ARDs retrieved by P1 + P2 |
|---|---|---|---|
| A baummanni | 8 | 2 | 8 |
| C koseri | 1 | 1 | 1 |
| C freundii | 14 | 2 | 12 |
| E aerogenes | 4 | 1 | 4 |
| E cloacae JRFQ01 | 9 | 1 | 9 |
| E cloacae JZY01 | 15 | 1 | 15 |
| E coli LFXU01 | 9 | 1 | 8 |
| E coli LHAT01 | 6 | 1 | 9 |
| K oxytoca | 9 | 2 | 9 |
| K pneumoniae LFBF01 | 7 | 1 | 7 |
| K pneumoniae CBWI01 | 15 | 3 | 13 |
| H influenzae | 1 | 0 | 1 |
| P mirabilis | 8 | 0 | 8 |
| P vulgaris | 12 | 1 | 12 |
| M morganii | 5 | 1 | 5 |
| P aeruginosa BADP01 | 9 | 8 | 9 |
| P aeruginosa JTVP01 | 10 | 9 | 10 |
| P stuartii | 5 | 0 | 5 |
| S aureus | 4 | 3 | 3 |
| S maltophilia | 4 | 3 | 4 |
| S marcescens | 5 | 2 | 5 |

Validation Study 2

In Table 2, one notes that both pipelines are able to retrieve the pathogen present in the sample, i.e. confirmed by classical microbiogical culture. However, Pipeline 1 never identifies any ARD, while the new pipeline identifies from 1 to 3 ARD by sample. ARD marked by an asterisk and confirmed to be link to the pathogen (some of reads mapping against the contig containing the ARD come from Kraken). Note that pipeline1 also identifies K. pneumoniae in sample 2. However, no 16S rDNA copy is found in the assembly and the size of the genome is 1.2 Mb, which is relatively small for a K. pneumonia genome (usually around 5 Mb), hence it might be a false positive.

TABLE 2

| | culture | Pipeline 1 | | New pipeline | |
|---|---|---|---|---|---|
| Sample | pathogens | pathogens | ARD | pathogens | ARD |
| 1 | E coli | E coli | | E coli | TEM-135* |
| 2 | H influenzae | H influenzae + K pneumoniae | | H influenzae | TEM-40 |
| 3 | S aureus | S aureus | | S aureus | mecA*, blaZ*, ANT(9)-1a |

Validation Study 3

In Table 3, one notes that both pipelines give very similar results and results coherent with classical microbiology, at least for identification results. Both pipelines give similar results, probably because the ARD retrieved are present in the reference sequences of the 2 pathogens, ie. AmpC must be present in the reference sequences of E. aerogenes, and ANT(9)-1A in the reference sequences of S aureus.

TABLE 3

| | classical microbiology | | Pipeline 1 | | New pipeline | |
|---|---|---|---|---|---|---|
| Sample | pathogens | AST profile | pathogens | ARD | pathogens | ARD |
| 1 | E aerogenes | resistance: amoxiciline, clavunalate intermediate resistance: cefuroxime | E aerogenes | AmpC_EAER* | E aerogenes | AmpC_EAER* |
| 2 | S aureus | resistance: peniciline, clindamycine | S aureus | ANT(9)-1A* | S aureus, S pneumoniae | ANT(9)-1A |

Figure 7:
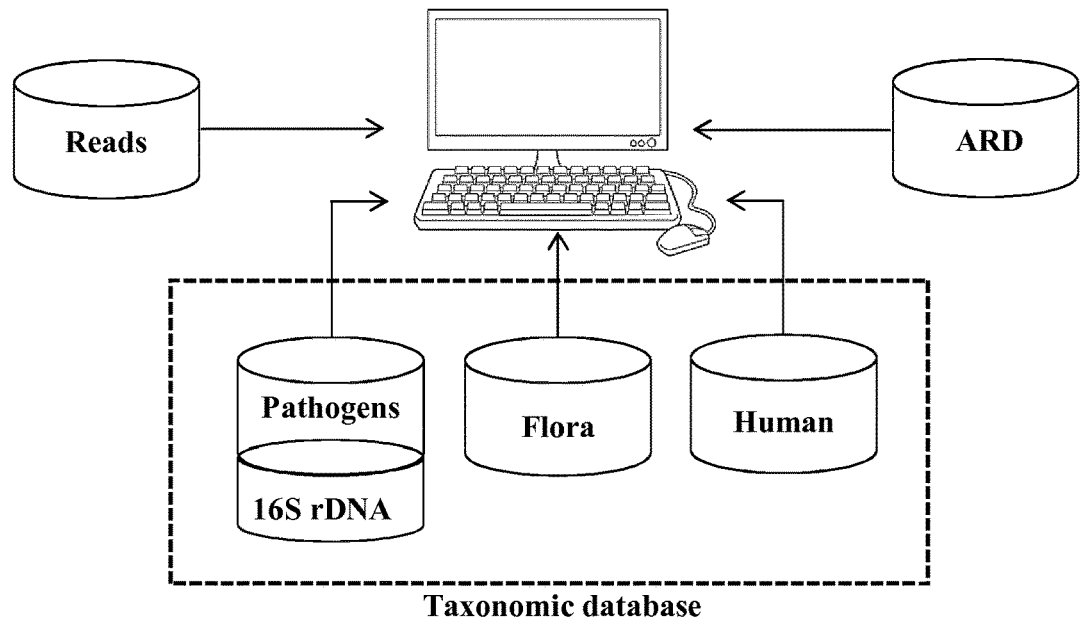
FIG. 7 is a schematic diagram illustrating a computer system for implanting the invention.

FIG. 7 illustrates a computer system carrying out the pipeline according to the invention. Said system comprises the databases described above (taxonomic database, ARD database) as well as database memorizing the reads. Those databases are connected to a computing unit, e.g. for example a personal computer, a tablet, a smartphone, a server, network of computers, and more generally any system comprising one or more microprocessors and/or one or more microcontrollers, e.g. a digital signal processor, and/or one more programmable logic device, configured to implement a digital processing the reads as described above. The computer unit comprises computer memories (RAM, ROM, cache memory, mass memory) for the storing the acquired distributions, instructions for executing the method according to the invention, and intermediate and final computation, in particular the list of pathogens and their linked ARD. The computer units further comprises a screen for displaying list and ARD.

The invention claimed is:

1. A method of analyzing a metagenomic sample, comprising:
processing the metagenomic sample to extract DNA from one or more pathogens if present in the metagenomic sample;
sequencing the extracted DNA to produce a set of digital nucleic acid sequences, i.e., "reads", that have an average length of L bp in which L>100;
assigning a first subset of reads to a known pathogen by mapping the first subset of reads against genomic data of the known pathogen using a first database comprising genomic data for a plurality of known pathogens;
assigning a second subset of reads to a sequence of a known antibiotic resistance determinant or virulence genetic determinant of a length greater than that of the average length of the reads by mapping the second subset of reads against sequence data of the known antibiotic resistance determinant or virulence genetic determinant using a second database comprising sequence data for a plurality of antibiotic resistance determinants and/or virulence genetic determinants such that there are (i) reads within the second subset of reads that fall entirely within the sequence of the known antibiotic resistance determinant or virulence genetic determinant and (ii) reads within the second subset of reads that are astride the sequence of the known antibiotic resistance determinant or virulence genetic determinant;
producing a pool of reads comprising the first subset of reads and the second subset of reads; and
assembling the reads in the pool in order to produce at least one assembled digital nucleic acid, i.e., "contig", wherein the reads that are astride the sequence of the known antibiotic resistance determinant or virulence genetic determinant each have (i) a first portion falling inside of the sequence and (ii) a second portion falling outside of the sequence in the range [1; L-50] bp.

2. The method of claim 1, wherein the antibiotic resistance determinant or virulence genetic determinant is a resistance gene or virulence gene, respectively.

3. The method of claim 1, further comprising annotating the contig after assembly of the contig using the second database or another database comprising sequence data for a plurality of antibiotic resistance determinants and/or virulence genetic determinants.

4. The method of claim 1, wherein:
the second database is an antibiotic resistance determinant (ARD) database comprising sequence data for a plurality of antibiotic resistance determinants; and
the second portion has a probability of right assignment against the ARD database that is greater than or equal to 70%.

5. The method of claim 1, wherein the reads of the second subset are mapped against the sequence data of the known antibiotic resistance determinant or virulence genetic determinant independently from each other.

6. The method of claim 1, wherein the metagenomic sample is a brochoalveolar lavage sample, urine sample, or blood sample.

7. The method of claim 1, wherein the metagenomic sample is a brochoalveolar lavage sample collected from a patient with ventilarory acquired pneumonia (VAP).

8. The method of claim 1, wherein the extracted DNA is sequenced by high throughput sequencing (HTS).

9. The method of claim 1, wherein the first portion falling inside of the sequence of the known antibiotic resistance determinant or virulence genetic determinant has a length that is at least 20 bp.

10. The method of claim 1, wherein the sequencing is a paired-end sequencing and, if a read assigned to the known antibiotic resistance determinant or virulence genetic determinant has a complementary read, the complementary read is also included within the pool of reads.

11. The method of claim 1, wherein the known antibiotic resistance determinant or virulence genetic determinant is determined to be part of the known pathogen's genome when:

$$D_{ARD} \in \left[\frac{1}{3} \times D_{path}; 3 \times D_{path}\right]$$

where $D_{ARD}$ is a median sequencing depth of the reads assigned to the known antibiotic resistance determinant or virulence genetic determinant and $D_{path}$ is a median sequencing depth of the reads assigned to the known pathogen.

12. The method of claim 1, wherein the genomic data for the plurality of known pathogens comprises 16SrDNA sequence and/or metaphlan2 data.

13. The method of claim 1, wherein the metagenomic sample is taken from a human or an animal, the first database further comprises flora and host genomic data, and reads mapped to the flora and host genomic data are filtered out.

14. A non-transitory computer readable medium storing instructions for executing a method performed by a computer, the method comprising:

assigning a first subset of reads to a known pathogen by mapping the first subset of reads against genomic data of the known pathogen using a first database comprising genomic data for a plurality of known pathogens;

assigning a second subset of reads to a sequence of a known antibiotic resistance determinant or virulence genetic determinant by mapping the second subset of reads against sequence data of the known antibiotic resistance determinant or virulence genetic determinant using a second database comprising sequence data for a plurality of antibiotic resistance determinants and/or virulence genetic determinants such that there are (i) reads within the second subset of reads that fall entirely within the sequence of the known antibiotic resistance determinant or virulence genetic determinant and (ii) reads within the second subset of reads that are astride the sequence of the known antibiotic resistance determinant or virulence genetic determinant;

producing a pool of reads comprising the first subset of reads and the second subset of reads; and assembling the reads in the pool in order to produce at least one assembled digital nucleic acid, i.e., "contig", wherein:

the metagenomic sample was processed to extract DNA from one or more pathogens if present in the metagenomic sample and the extracted DNA was sequenced to produce a set of digital nucleic acid sequences, i.e., "reads", that have an average length of L bp in which L>100;

the sequence of the known antibiotic resistance determinant or virulence genetic determinant has a length that is greater than that of the average length of the reads;

and the reads that are astride the sequence of the known antibiotic resistance determinant or virulence genetic determinant each have (i) a first portion falling inside of the sequence and (ii) a second portion falling outside of the sequence in the range [1; L-50] bp.

15. The non-transitory computer readable medium of claim 14, wherein the antibiotic resistance determinant or virulence genetic determinant is a resistance gene or virulence gene, respectively.

16. The non-transitory computer readable medium of claim 14, wherein the method further comprises annotating the contig after assembly of the contig using the second database or another database comprising sequence data for a plurality of antibiotic resistance determinants and/or virulence genetic determinants.

17. The non-transitory computer readable medium of claim 14, wherein:

the second database is an antibiotic resistance determinant (ARD) database comprising sequence data for a plurality of antibiotic resistance determinants; and the second portion has a probability of right assignment against the ARD database that is greater than or equal to 70%.

18. The non-transitory computer readable medium of claim 14, wherein the reads of the second subset are mapped against the sequence data of the known antibiotic resistance determinant or virulence genetic determinant independently from each other.

19. The non-transitory computer readable medium of claim 14, wherein the first portion falling inside of the sequence of the known antibiotic resistance determinant or virulence genetic determinant has a length that is at least 20 bp.

20. The non-transitory computer readable medium of claim 14, wherein the known antibiotic resistance determinant or virulence genetic determinant is determined to be part of the known pathogen's genome when:

$$D_{ARD} \in \left[\frac{1}{3} \times D_{path}; 3 \times D_{path}\right]$$

where $D_{ARD}$ is a median sequencing depth of the reads assigned to the known antibiotic resistance determinant or virulence genetic determinant and $D_{path}$ is a median sequencing depth of the reads assigned to the known pathogen.

* * * * *